US00PP18358P2

(12) United States Plant Patent
Okawa

(10) Patent No.: US PP18,358 P2
(45) Date of Patent: Dec. 25, 2007

(54) ***ANGELONIA* PLANT NAMED 'FAIRY QUEEN'**

(50) Latin Name: *Angelonia salicariifolia*
Varietal Denomination: Fairy Queen

(76) Inventor: Michinori Okawa, 10, Mutsure, Tahara-city, Aichi, 441-3413 (JP)

( * ) Notice: Subject to any disclaimer, the term of this patent is extended or adjusted under 35 U.S.C. 154(b) by 0 days.

(21) Appl. No.: 11/499,638

(22) Filed: Aug. 5, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Angelonia* plant named 'Fairy Queen', characterized by its upright and vigorous plant habit; medium green-colored foliage; pink and white bi-colored flowers; and good garden performance.

2 Drawing Sheets

Botanical designation: *Angelonia salicariifolia.*
Cultivar denomination: 'Fairy Queen'.

BACKGROUND OF THE INVENTION

The present invention relates to a new and distinct cultivar of *Angelonia,* botanically known as *Angelonia salicariifolia* and hereinafter referred to by the name 'Fairy Queen'.

The new *Angelonia* is a naturally-occurring branch mutation of an unnamed selection of *Angelonia salicariifolia,* not patented. The new *Angelonia* was discovered by the Inventor from within a population of plants of the parent selection in a controlled environment in Aichi, Japan in July, 2004.

Asexual reproduction of the new *Angelonia* by cuttings in a controlled environment in Aichi, Japan since July, 2004, has shown that the unique features of this new *Angelonia* are stable and reproduced true to type in successive generations.

SUMMARY OF THE INVENTION

The cultivar Fairy Queen has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fairy Queen'. These characteristics in combination distinguish 'Fairy Queen' as a new and distinct cultivar of *Angelonia:*

1. Upright and vigorous plant habit.
2. Medium green-colored foliage.
3. Pink and white bi-colored flowers.
4. Good garden performance.

Plants of the new *Angelonia* differ from plants of the parent selection primarily in flower color as plants of the parent selection have pink-colored flowers.

Plants of the new *Angelonia* can be compared to plants of the cultivar Anstern, disclosed in U.S. Plant Pat. No. 13,143. Plants of the new *Angelonia* and the cultivar Anstern differ in the following characteristics:

1. Plants of the new *Angelonia* have smaller leaves and flowers than plants of the cultivar Anstern.
2. Plants of the new *Angelonia* and the cultivar Anstern differ in flower color as plants of the cultivar Anstern have blue and white bi-colored flowers.

Plants of the new *Angelonia* can also be compared to plants of the cultivar Anpink, disclosed in U.S. Plant Pat. No. 16,818. Plants of the new *Angelonia* and the cultivar Anpink differ in the following characteristics:

1. Plants of the new *Angelonia* have smaller flowers than plants of the cultivar Anpink.
2. Plants of the new *Angelonia* and the cultivar Anpink differ in flower color as plants of the cultivar Anpink have pink-colored flowers.

BRIEF DESCRIPTION OF THE PHOTOGRAPHS

The accompanying colored photograph illustrates the overall appearance of the new *Angelonia,* showing the colors as true as it is reasonably possible to obtain in colored reproductions of this type. Colors in the photograph may differ slightly from the color values cited in the detailed botanical description which accurately describe the colors of the new *Angelonia.*

The photograph on the first sheet comprises a side perspective view of a typical flowering plant of 'Fairy Queen' grown in a container.

The photograph on the second sheet is a close-up view of a typical flower of 'Fairy Queen'.

DETAILED BOTANICAL DESCRIPTION

The aforementioned photographs and following observations, measurements and values describe plants grown in Aichi, Japan, under commercial practice in a glass-covered greenhouse with day temperatures ranging from 20° C. to 30° C., night temperatures averaging 20° C. and light levels about 50 Kilolux. Plants had been growing for about twenty weeks when the photographs and description were taken. In the following description, color references are made to The Royal Horticultural Society Colour Chart, 2001 Edition, except where general terms of ordinary dictionary significance are used.

Botanical classification: *Angelonia salicariifolia* cultivar Fairy Queen.

Parentage: Naturally-occurring branch mutation of an unnamed selection of *Angelonia salicariifolia,* not patented.

Propagation:

*Type.*—By cuttings.

*Time to initiate roots.*—About 15 days at 20° C. to 30° C.

*Time to produce a rooted young plant.*—About one month at 20° C. to 30° C.

*Root description.*—Moderately thick, fibrous; color, 160C.

*Rooting habit.*—Moderate branching; moderately dense.

Plant description:

*Plant form/habit.*—Herbaceous perennial. Upright and vigorous plant habit; inverted triangle. Freely branching habit.

*Plant height.*—About 40 cm to 60 cm.

*Plant width* (*spread*).—About 25 cm.

*Lateral branches.*—Length: About 50 cm. Diameter: About 4.5 mm. Internode length: About 2.5 cm. Strength: Moderately strong. Texture: Smooth, glabrous. Color: 144B.

Foliage description:

*Arrangement.*—Opposite, simple; sessile.

*Length.*—About 7 cm.

*Width.*—About 8 mm.

*Shape.*—Linear.

*Apex.*—Cuspidate.

*Margin.*—Serrate.

*Texture, upper surface.*—Smooth, glabrous.

*Texture, lower surface.*—Pubescent.

*Venation pattern.*—Pinnate.

*Color.*—Developing leaves, upper surface: 144A. Developing leaves, lower surface: 148A. Fully expanded leaves, upper surface: 146B; venation, 148A. Fully expanded leaves, lower surface: 135A; venation, 150D.

Flower description:

*Flower type/habit.*—Single flowers arranged in terminal racemes; flowers face mostly outward. Freely flowering habit with about 320 flower buds and flowers developing per plant.

*Fragrance.*—Strong; lemon-like.

*Natural flowering season.*—Continuously flowering from May through October in Japan. Flowers persistent.

*Postproduction longevity.*—Flowers last about four to seven days on the plant.

*Flower buds.*—Height: About 4.8 mm. Diameter: About 3.2 mm. Shape: Globular. Color: 4D.

*Inflorescence height.*—About 15 cm.

*Inflorescence diameter.*—About 4 cm.

*Flower diameter.*—About 1.8 cm by 1.9 cm.

*Flower depth.*—About 3 mm.

*Petals.*—Quantity per flower: Typically five in a single whorl; petals fused at the base. Length: About 7 mm. Width: About 7 mm. Shape: Obovate. Apex: Rounded; emarginate. Margin: Entire. Texture, upper and lower surfaces: Smooth, glabrous. Color: When opening, upper and lower surfaces: 155B; stripes, 55B. Fully opened, upper and lower surfaces: 155B; stripes, 55B.

*Sepals.*—Quantity per flower: Typically five in a single whorl. Length: About 2.7 mm. Width: About 1 mm. Shape: Lanceolate. Apex: Acute. Margin: Entire. Texture, upper and lower surfaces: Smooth, glabrous. Color, upper and lower surfaces: 143A.

*Pedicels.*—Length: About 1.3 cm. Diameter: About 2 mm. Strength: Moderately strong. Texture: Smooth, glabrous. Color: 146A.

*Reproductive organs.*—Stamens: Quantity per flower: Typically four. Filament length: About 2.2 mm. Filament color: 155B. Anther length: About 0.1 mm. Anther color: 158B. Pollen amount: Scarce. Pollen color: 158B. Pistils: Quantity per flower: One. Pistil length: About 2.3 mm. Stigma shape: Tapering. Stigma color: 156D.

*Seed/fruit.*—Seed and fruit development have not been observed.

Disease/pest resistance: Plants of the new *Angelonia* have not been noted to be resistant to pathogens and pests common to *Angelonia.*

Garden performance: Plants of the new *Angelonia* have been observed to have good garden performance and tolerate rain, wind and temperatures ranging from 10° C. to 35° C.

It is claimed:

1. A new and distinct *Angelonia* plant named 'Fairy Queen' as illustrated and described.

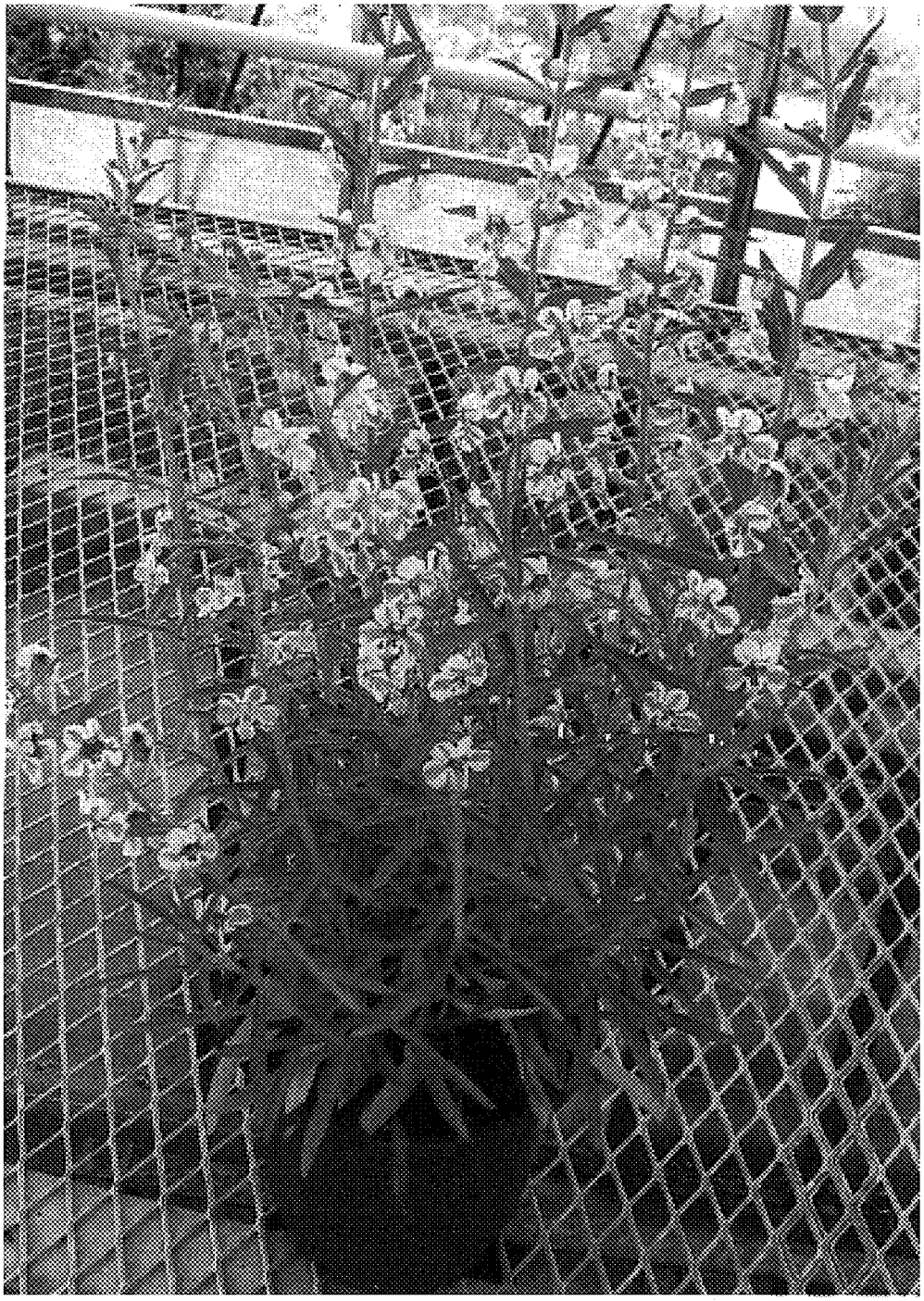

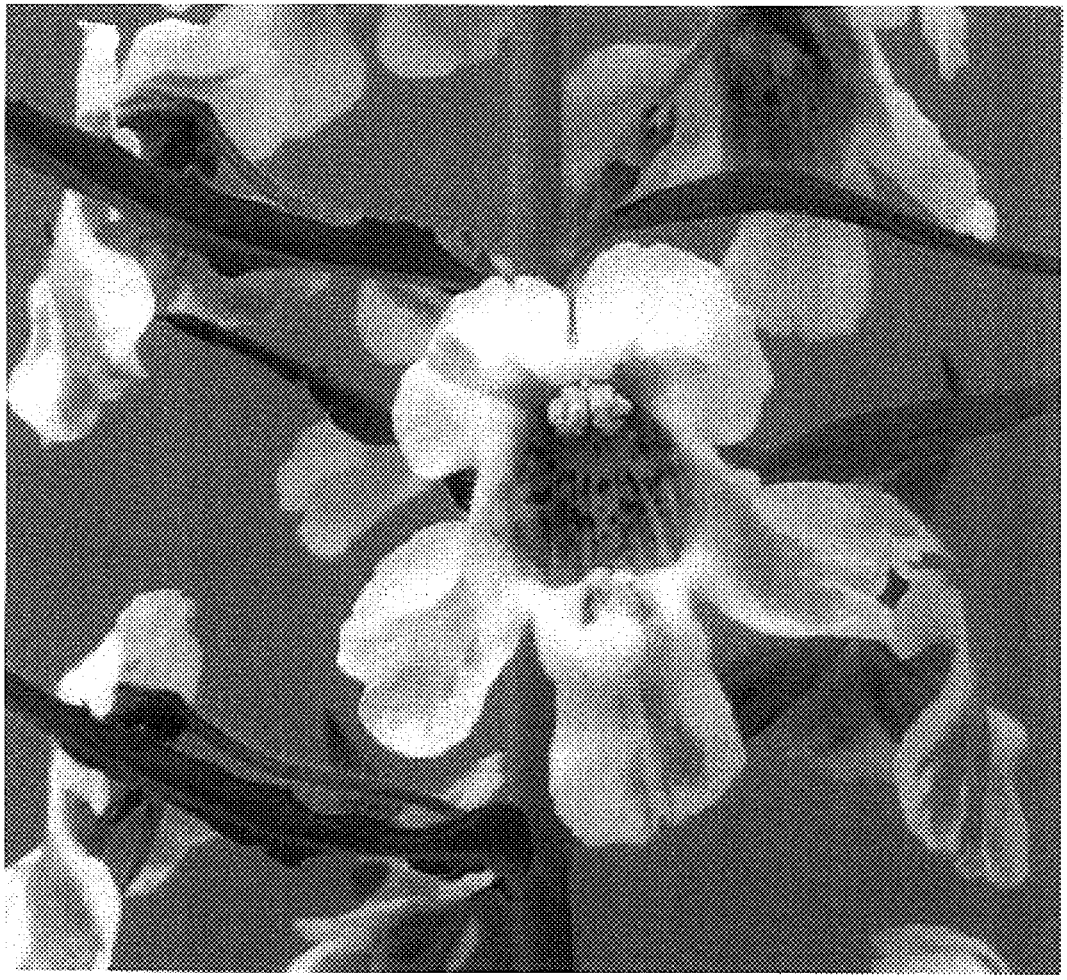

* * * * *